(12) United States Patent
Thoen

(10) Patent No.: US 9,724,247 B2
(45) Date of Patent: Aug. 8, 2017

(54) SENSOR, AN INCONTINENCE GARMENT, AND A METHOD FOR ACTIVATING AN INCONTINENCE GARMENT

(71) Applicant: NXP B.V., Eindhoven (NL)

(72) Inventor: Steven Thoen, Leuven (BE)

(73) Assignee: NXP B.V., Eindhoven (NL)

( * ) Notice: Subject to any disclaimer, the term of this patent is extended or adjusted under 35 U.S.C. 154(b) by 0 days.

(21) Appl. No.: 14/697,989

(22) Filed: Apr. 28, 2015

(65) Prior Publication Data

US 2015/0320609 A1    Nov. 12, 2015

(30) Foreign Application Priority Data

May 7, 2014    (EP) ..................................... 14167303

(51) Int. Cl.
*A61F 13/42*    (2006.01)

(52) U.S. Cl.
CPC ........ *A61F 13/42* (2013.01); *A61F 2013/424* (2013.01)

(58) Field of Classification Search
CPC .. A61F 13/42; A61F 2013/424; G01N 27/048
USPC ...................................................... 340/573.5
See application file for complete search history.

(56) References Cited

U.S. PATENT DOCUMENTS

| | | | | |
|---|---|---|---|---|
| 4,488,097 A | * | 12/1984 | MacLaughlin | ........... F16P 3/20 318/443 |
| 5,760,694 A | * | 6/1998 | Nissim | ..................... A61F 13/42 128/885 |
| 2002/0070864 A1 | * | 6/2002 | Jeutter | ..................... A61F 13/42 340/573.1 |
| 2004/0207530 A1 | * | 10/2004 | Nielsen | .................... A61F 13/42 340/604 |
| 2008/0262453 A1 | | 10/2008 | McGinnis et al. | |
| 2008/0266117 A1 | * | 10/2008 | Song | ........................ A61F 13/42 340/573.5 |
| 2015/0087935 A1 | * | 3/2015 | Davis | ................. A61B 5/14532 600/309 |

FOREIGN PATENT DOCUMENTS

| | | |
|---|---|---|
| DE | 102010053789 A1 * | 6/2012 |
| EP | 1 063 624 A1 | 12/2000 |
| WO | WO-2006/051426 A2 | 5/2006 |

OTHER PUBLICATIONS

Extended European Search Report for Application No. 14176389.6 (Oct. 19, 2015).

* cited by examiner

*Primary Examiner* — Omer S Khan

(57) ABSTRACT

There is disclosed herein a sensor for detecting at least one of urination and excretion into an incontinence garment, the sensor comprising an activation unit and a sensing unit and being connectable to a power supply; the activation unit comprising: two spaced-apart electrodes, and a switch arranged in series between the sensing unit and the power supply; wherein the activation unit is configured to activate the sensing unit in the presence of moisture by closing the switch; and wherein at least one of the sensing unit and the activation unit comprises a latching circuit arranged such that the activation of the sensing unit is irreversible. An incontinence garments such as the diaper is incorporating such a sensor is also disclosed as it is a method for operating such a sensor or incontinence garment.

15 Claims, 2 Drawing Sheets

SENSOR, AN INCONTINENCE GARMENT, AND A METHOD FOR ACTIVATING AN INCONTINENCE GARMENT

CROSS-REFERENCE TO RELATED APPLICATIONS

This application claims the priority under 35 U.S.C. §119 of European patent application no. 14167303.8, filed on May 7, 2014, the contents of which are incorporated by reference herein.

FIELD

This invention relates to sensors, incontinence garments, and to methods of activating incontinence garments.

BACKGROUND

Due to ageing populations in many regions of the world, there is an increasing use of incontinence garments. Changing of incontinence garments such as diapers when they become saturated with urine, or fouled due to excrement—stools or faeces, is a basic aspect of health care for incontinent patients. It is important to know when it is necessary to change the diaper: on the one hand, changing diapers more often than is necessary is expensive and wasteful of diaper materials and care-worker effort, and overly intrusive and disruptive; on the other hand if a diaper is not changed at an appropriate time, there is a significant risk of skin irritation which may lead to the requirement for further medical intervention and treatment which may take several weeks, and be more disruptive and expensive. Additionally, by providing timely alerts, leakage resulting in soiled bed linen and clothing can be avoided resulting in savings in labour and expenses.

Odour or touch may be used to detect the fouling of a diaper; in all but the worst cases this may require close inspection: whereas with infants, this may be acceptable, with adult and elderly patients it may be considered to be intrusive. It would therefore be desirable to provide automated systems for providing an appropriate alert when a diaper is required to be changed.

Recently, it has been proposed to incorporate electronics into incontinence garments, so as to determine when the garment becomes wet or soiled, to produce so-called "smart-diapers" and the like. For example U.S. patent application publication number US2008/0262453 discloses a remote monitoring diaper system, kits and method of using the same, which includes a remotely placed monitor station in communication with a diaper device. The diaper device has electronic components that are configured to detect an increase in conductivity across opposing detector electrodes, which increase can then be used to indicate, via an EMF signal, that the diaper device is wet.

Incontinence garments, particularly for the elderly are conventionally "long-shelf-life" articles, in that they are often manufactured and supplied in bought in bulk quantities to the user such as a care home, and may not be used for months or even years. For smart diapers and other incontinence garments incorporating electronics, this introduces a potential risk that the power supply for the electronics may deteriorate between manufacture of the garment and use of the electronics to detect soiling or the like.

SUMMARY

According to an aspect there is disclosed a sensor for detecting at least one of urination and excretion into an incontinence garment such as a diaper, the sensor comprising an activation unit and a sensing unit and being connectable to a power supply; the activation unit comprising: at least two spaced-apart electrodes, and a switch arranged in series with the sensing unit and being for connecting the sensing unit to a power supply; wherein the activation unit is configured to activate the sensing unit in the presence of moisture by closing the switch; and at least one of the sensing unit and the activation unit comprises a latching circuit. arranged such that the activation of the sensing unit is irreversible. Activation of the sensing unit generally changes its status from one of being dormant or inactive, into one of being active. The power supply may be a battery, and the battery may be integral to the incontinence garment.

In embodiments, the latching circuit is arranged such that the activation of the sensing unit is irreversible. In other embodiments the latching is for a fixed, or variable period of time at the end, of which the sensing unit is deactivated. Deactivation may be allowed or effected as the result of, for instance and without limitation, detection of a false positive, or the receipt of an acknowledgement of an alert signal, or a manual reset—for example in the event that an incontinence garment in storage becomes damp, and a user wishes to extend its shelf-life. Provision of an activation unit provide for decoupling the operation of the sensing unit from the presence of moisture in incontinence garment. Operation of the sensing unit may thus be non-transitory, or permanent, in the sense that it is not limited to a period when there is moisture present.

In one or more embodiments the activation unit is configured to detect a change in electrical conductance between the two spaced-apart electrodes.

In one or more other embodiments the two electrodes are dissimilar and have different electrochemical potential so as to form an electrochemical cell in the presence of urine, and the activation unit is powered by the electrochemical cell.

In one or more embodiments the at least two spaced-apart electrodes are switchably contactable to the sensing unit.

In one or more embodiments the activation unit is configured to latch the switch closed, upon activation. In one or more embodiments the sensor further comprises a holding circuit for holding the switch closed upon activation, wherein the holding circuit is powered by the power supply. The holding circuit may be configured so as to be powered only after activation.

According to another aspect there is provided an incontinence garment comprising a sensor according to any preceding claim, and a power supply. The power supply may be a battery which may be integral to the incontinence garment. The incontinence garments may be a diaper. The incontinence garment may include a wireless transmitter for directly or indirectly alerting a care working on the occurrence of soiling the garment.

According to yet another aspect to those provided a method of activating a sensor for an incontinence garment, the sensor comprising an activation unit and a sensing unit and being connectable to a power supply, the activation unit comprising: two spaced-apart electrodes, and a switch arranged in series between the sensing unit and the power supply, the method comprising activating the sensing unit in the presence of moisture by closing the switch, and latching at least one of the sensing unit and the activation unit. The activation of the sensing unit may be irreversible.

In one or more embodiments closing the switch comprises providing a change in electrical conductance between the two spaced-apart electrodes to result in an effective short-circuit.

In one or more other embodiments, the two electrodes are dissimilar and have different electrochemical potentials so as to form an electrochemical cell in the presence of urine, and the step of activating the sensing unit in the presence of moisture by closing the switch is enabled by power from the electrochemical cell.

BRIEF DESCRIPTION OF DRAWINGS

Embodiments of the invention will be described, by way of example only, with reference to the drawings, in which.

Figure 1:
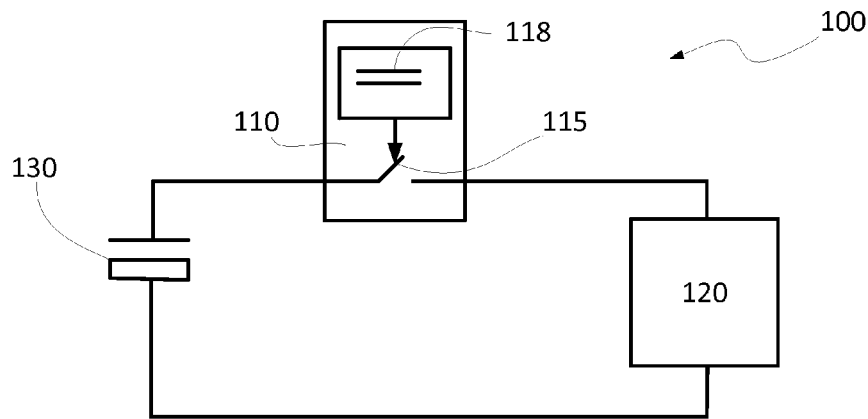
FIG. 1 shows a simplified block diagram of a sensor according to embodiments.

It should be noted that the figures are diagrammatic and not drawn to scale. Relative dimensions and proportions of parts of these Figures have been shown exaggerated or reduced in size, for the sake of clarity and convenience in the drawings. The same reference signs are generally used to refer to corresponding or similar feature in modified and different embodiments

DETAILED DESCRIPTION OF EMBODIMENTS

FIG. 1 shows a simplified block diagram of a sensor 100 according to embodiments. The sensor comprises an activation unit 110 and a sensing unit 120. The activation unit 110 includes a switch 115 which is arranged so as to be able to switchably connect the sensor unit 120 to a power supply 130. Typically the power supply 130 is in the form of a battery.

The activation unit 110 includes a pair of electrodes 118. These are shown schematically in the figure as being distinct or separate from the switch 115; however, in some embodiments the electrodes may form an integral part of the switch 115.

Figure 2A:
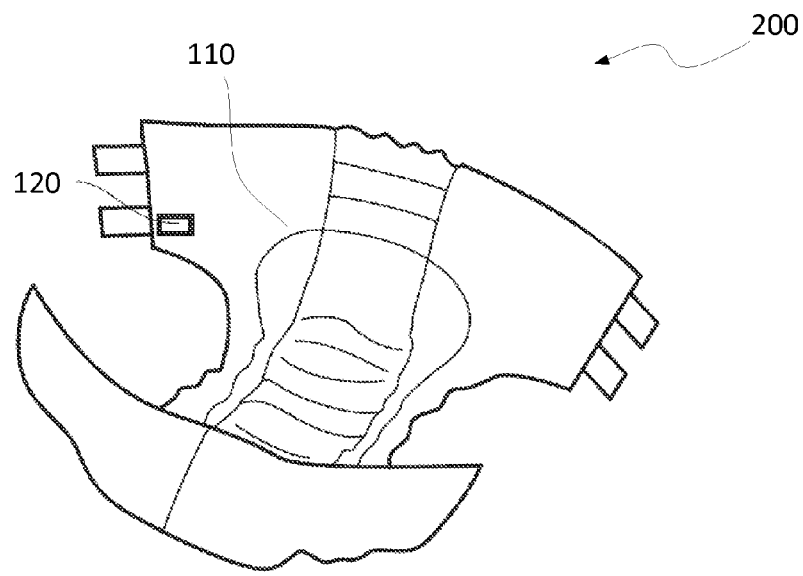
FIG. 2a shows an perspective view of a smart diaper.
Figure 2B:
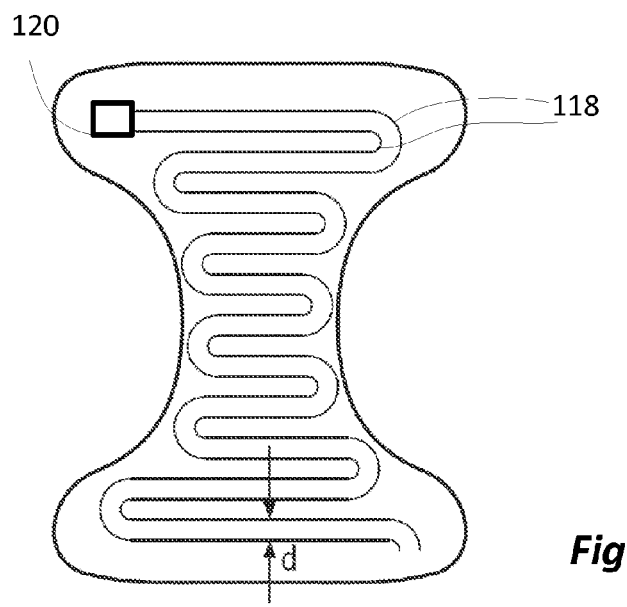
FIG. 2b shows, in plan view an example of sensor including an arrangement of a pair of electrodes covering part of the surface of a diaper.

Turning now to FIG. 2, this shows at FIG. 2a a perspective view of a smart diaper 200 according to embodiments, and at FIG. 2b, in plan view, an example of sensor including an arrangement of a pair of electrodes 118 covering part of the surface of the diaper 200.

Smart diaper 200 includes a sensor 100, having a sensing unit 120 and activation unit 110. Although the sensing unit may be discrete as shown, in other embodiments, the sensing unit is distributed across the incontinence garment or smart diaper 200, As shown in FIG. 2b the activation unit 110 includes a pair of electrodes 118, which may be distributed over the inner surface of the diaper. The electrodes may be distributed over some or all of the inner surface of the diaper. The position and spacing of the electrodes is such that when a wearer of diaper urinates or passes excrement, the moisture in the urine or excrement forms a liquid bridge between the two electrodes. The electrodes may typically be spaced apart by a distant d which may be between approximately 0.1 to 10 mm, and in typical applications may be of the order of 0.5 to 3 mm.

In operation, the presence of moisture between the electrodes 118 is used to close the switch 115. In one or more embodiments, the resultant change in conductance between the electrodes is sensed. The change in conductance due to the presence of moisture may result in a simple short-circuit between the electrodes, thus closing the switch. The sensor unit may then be supplied with power from the power supply, and thereby become activated. In order to ensure that the sensing unit 120 remains activated once the presence of moisture has been detected, a latching arrangement may be required. Otherwise, particular in the example case of a "feel-dry" diaper, the sensing unit may be disabled, once the moisture is absorbed into the diaper material.

Figure 3:
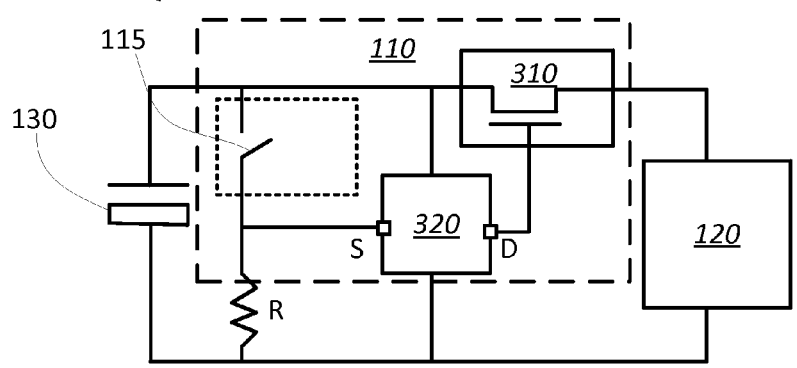
FIG. 3 shows a block diagram of a sensor including a latching arrangement.

FIG. 3 shows a block diagram of a sensor 300 including a latching circuit or arrangement as part of the activation unit 110. The sensor 300 includes a sensing unit 120, and may be connectable to a battery 130 by means of a controllable switch 310, which in this instance is shown as a MOSFET. In other embodiments, other switches may be used, such as bipolar, or p-mos, transistors. The control terminal of controllable switch 310 is connected to a set reset flip-flop 320. An output D of the set reset flip-flop is connected, in operation, to the battery 130, in order to provide power to operate the set reset flip-flop. The set input S of the set reset flip-flop 320 is connectable to the battery 130 through switch 115. The set input is also connected to ground by a biasing resistor R in order to prevent the input from floating. In other embodiments, the set reset flip-flop may be replaced by, for instance and without limitation, by a pair of back-to-back switches in a bistable configuration.

In embodiments, switch 115 is comprised of the pair of electrodes 118, and in operation the switch is closed by the introduction of moisture between the electrodes providing an effective short-circuit, as described above. Provided that the resistance of this effective short-circuit is appropriately lower than the resistance of biasing resistor R, then the set input S to set reset flip-flop 320 will go high, and so its output will also go high, and since the output is connected to the control terminal of controllable switch 310, controllable switch 310 is thereby switched on, that is to say, closed. The sensor unit 120 is thereby activated by being connected the battery 130. As shown, there is no controllable reset input to the set reset flip-flop—typically this input would be grounded—and as a result, the activation of the sensor unit 120 is permanent or irreversible. In other embodiments, the reset may be connected to a state machine in the sensing unit to disable the sensing for instance after false triggering or after a fixed time period, or a variable time period, for instance after the measurement is done. In such embodiments a subsequent urination may then re-activate the sensor, allowing for a subsequent measurement.

Thus, in such embodiments, any galvanic contact of the activation switch may be automatically de-bounced by the set reset flip-flop, and the series impedance between the sensor unit and the battery may be well controlled.

It will be appreciated that in embodiments such as those described above, a generally small amount of current may be drawn from the battery 130 prior to activation of the sensor unit 120. This current may be required to provide power to the set reset flip-flop. In addition, there may be a small residual current due to finite but nonzero conductivity between the electrodes prior to the introduction of the short-circuit by moisture.

Figure 4:
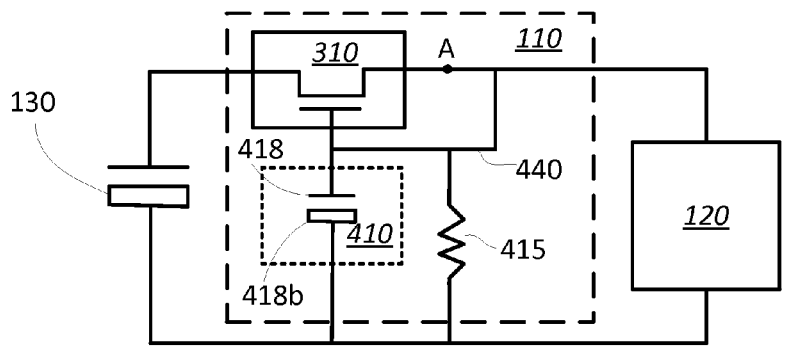
FIG. 4 shows a block diagram of another sensor including a self-latching arrangement.

FIG. 4 shows a block diagram of another sensor including a self-latching arrangement. Similarly to the arrangement shown in FIG. 3, a controllable switch 310 is arranged in series between the switching it unit 120 and a battery 130. However, in this arrangement instead of a change in conductivity, the galvanic action of urine between dissimilar metals is utilised: in this and similar embodiments, the electrodes 118 are formed of dissimilar materials 418a and 418b. Provided that the materials have different electrochemical potentials, in the presence of urine as an electrolyte, the electrodes and urine may form an electrochemical cell 410. The electrochemical cell is connected to the control terminal of the controllable switch 310 such that the controllable switch 310 is switched on or closed as a result of urine being introduced between dissimilar electrodes 418a and 418b. The arrangement may be made to latch "on" by connecting the control terminal of the controllable switch to its output, shown at A, as shown at 440. A high-value resistor 415, such as 10 MΩ, to ground may be included to prevent floating lines. The skilled person would appreciate that in other embodiments, a set reset flip-flop may be used instead of the connection 440. Provided the set reset flip-flop is connected on the output side of the controllable switch 310, it may be arranged that no current is required by the flip-flop prior to activation.

Thus, in embodiments such as those shown in FIGS. 2 and 4, it may be arranged that prior to activation of the sensing unit 120, no current is drawn from the battery 130 whatsoever. It will be immediately apparent that in such an arrangement the shelf-life of the diaper is maximised.

Although as shown in FIG. 4, the electrochemical cell formed from the electrodes and urine is arranged to directly enable the controllable switch, in other embodiments of the electrochemical cell may be arranged so as to provide power to a more complex activation unit, such as one including a set reset flip-flop as described above, the power for which may be drawn from or provided by the electrochemical cell. In other embodiments, the activation unit may include a threshold detector, so as to avoid activating in the presence of a low level of moisture, such as may be produced by the sweat of a wearer of the incontinence garment.

The sensor unit may provide smart sensing functionality: for instance it may be possible to detect when the diaper is saturated with urine, or when a wearer of the diaper has excreted into the diaper. When the sensor unit is combined with a diaper such as a "stay-dry" or "feel-dry" diaper, which rapidly transports urine away from the inner surface, it may be possible to distinguish between different forms of fouling, such as excrement and urine. The sensor unit may further comprise a transmitter to transmit the results of the sensing to a receiver, for instance in order to alert a nurse or other care worker, on the occurrence of soiling or fouling of the diaper. Such a diaper with the sensing functionality may be described as a smart diaper.

Although the electrodes shown in FIG. 2b are depicted as a meandering pair of electrodes with a relatively constant distance d therebetween, the skilled person would appreciate that alternative arrangements of electrodes are equally possible: in one example (not shown), the pair of electrodes may each comprise a series of fingers attached to a central spine, and the fingers of the two electrodes may be inter-digitated. Other forms of meander may be used in addition or alternatively; for instance the parallel tracks may be arranged to follow the contours of the perimeter of the diaper and spiral in towards the centre.

The electrodes may be provided by being printed onto a single surface of one layer in a multilayer stack or laminate which forms the outward facing surface region of the diaper. As a non-limiting alternative, the tracks may be provided by being woven into a material which forms a layer of a multilayer stack or laminate. As a further non-limiting alternative, the electrodes may be deposited conductive material, rather than printed or woven material.

In each of these non-limiting examples, the electrodes may be considered to be planar, since the separation is generally in the same plane and the electrodes are on or in the same layer of material. In other embodiments, the electrodes may be non-planar or multi-planar, or may be arranged in different planes. For instance, the first electrode 118 or 418a may be arranged with fingers extending in both directions from a central spine, or bus. This electrode may be arranged in a single plane, which may be one surface of a layer of a laminate or stacked structure. In a separate plane, which may be the opposite surface of the same layer, or may be a surface of another layer in a laminate or stacked structure, is arranged the other electrode 118 or 418b. The second electrode may also be arranged as a central spine, or bus, extending from which on both sides are fingers. The construction—that is so say the materials or dimensions—of the central spine or bus of each electrode may be the same as, or different from, the fingers. In particular in the case that they are different, it may be possible to determine spatial gradients over the diaper surface.

The above embodiments have been described with reference to diapers as the incontinence garments. It will be appreciated that other incontinence garments such as sanitary pads may be used instead of diapers. Further, it will be appreciated that the diaper or other incontinence garment may transmit its alert signal only to a nearby receiver, which will in general be that worn by the patient themselves. Identification information as to which patient requires care may thus not need to be embedded in the alert signal from the diaper to the receiver, since this information can be added by the receiver before forwarding the alert as a soiling alert.

From reading the present disclosure, other variations and modifications will be apparent to the skilled person. Such variations and modifications may involve equivalent and other features which are already known in the art of smart incontinence garments, and which may be used instead of, or in addition to, features already described herein.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The applicant hereby gives notice that new claims may be formulated to such features and/or combinations of such features during the prosecution of the present application or of any further application derived therefrom.

For the sake of completeness it is also stated that the term "comprising" does not exclude other elements or steps, the term "a" or "an" does not exclude a plurality, a single processor or other unit may fulfil the functions of several means recited in the claims and reference signs in the claims shall not be construed as limiting the scope of the claims.

The invention claimed is:

1. A sensor apparatus included in an incontinence garment, the sensor apparatus comprising:
an activation unit and a sensing unit and being connectable to a power supply, the activation unit comprising:
at least two spaced-apart electrodes; and a controllable switch arranged in series with the sensing unit and configured to connect the sensing unit to the power supply, wherein the activation unit is configured to activate the sensing unit in a presence of at least one of, moisture, urination or excretion, and wherein at least one of the sensing unit and the activation unit comprises a latching circuit configured to close the controllable switch.

2. The sensor apparatus as claimed in claim 1, wherein the latching circuit is arranged such that the activation of the sensing unit is irreversible.

3. The sensor apparatus as claimed in claim 1, wherein the activation unit is configured to detect a change in electrical conductance between the two spaced-apart electrodes.

4. The sensor apparatus as claimed in claim 1, wherein the two electrodes are dissimilar and have different electrochemical potentials so as to form an electrochemical cell in the presence of urine, and the activation unit is powered by the electrochemical cell.

5. The sensor apparatus as claimed in claim 1, wherein the at least two spaced-apart electrodes are switchably contactable to the sensing unit.

6. The sensor apparatus as claimed in claim 1, wherein the activation unit is configured to latch the controllable switch closed, upon activation.

7. The sensor apparatus as claimed in claim 1, wherein the latching switch is configured to hold the controllable switch closed upon activation, wherein the latching switch is powered by the power supply.

8. The sensor apparatus as claimed in claim 7, wherein the latching switch is configured so as to be powered only after activation.

9. An incontinence garment comprising:
 a sensor apparatus including,
  an activation unit and a sensing unit and being connectable to a power supply;
  the activation unit comprising:
   at least two spaced-apart electrodes; and
   a controllable switch arranged in series with the sensing unit and configured to connect the sensing unit to the power supply,
  wherein the activation unit is configured to activate the sensing unit in a presence of at least one of, moisture, urination or excretion, and wherein at least one of the sensing unit and the activation unit comprises a latching circuit configured to close the controllable switch.

10. The incontinence garment as according to claim 9, wherein the power supply is a battery which is integral to the incontinence garment.

11. The incontinence garment according to claim 9, wherein the sensor is included in a diaper.

12. A method of activating a sensor apparatus included in an incontinence garment,
 the sensor apparatus comprising an activation unit and a sensing unit and being connectable to a power supply,
 the activation unit comprising:
  two spaced-apart electrodes, and
  a controllable switch arranged in series between the sensing unit and the power supply;
 the method comprising activating the sensing unit in a presence of at least one of, moisture, urination or excretion, and latching at least one of the sensing unit and the activation unit by closing the controllable switch.

13. The method of claim 12, wherein the activation of the sensing unit is irreversible.

14. The method of claim 12, wherein closing the controllable switch comprises providing a change in electrical conductance between the two spaced-apart electrodes to result in an effective short-circuit.

15. The method of claim 12, wherein the two electrodes are dissimilar and have different electrochemical potentials so as to form an electrochemical cell in the presence of urine, and the step of activating the sensing unit in the presence of moisture by closing the controllable switch is enabled by power from the electrochemical cell.

* * * * *